United States Patent [19]
Schmitz

[11] Patent Number: 5,620,421
[45] Date of Patent: Apr. 15, 1997

[54] SYRINGE INJECTOR SYSTEM

[76] Inventor: William L. Schmitz, 43901 Citrus View Dr., Hemet, Calif. 92344

[21] Appl. No.: 287,674

[22] Filed: Aug. 8, 1994

Related U.S. Application Data

[63] Continuation-in-part of Ser. No. 164,330, Dec. 9, 1993.

[51] Int. Cl.$^6$ ............................................. A61M 5/178
[52] U.S. Cl. ................................... 604/135; 604/138
[58] Field of Search ................................. 604/131–139, 604/110, 195, 196, 232

[56] References Cited

U.S. PATENT DOCUMENTS

| | | | |
|---|---|---|---|
| 3,403,680 | 10/1968 | Sinclair et al. | 604/138 |
| 3,556,100 | 1/1971 | Hurschman | 604/138 |
| 4,767,413 | 8/1988 | Haber et al. | 604/198 |
| 4,968,302 | 11/1990 | Schluter et al. | 604/135 |
| 5,041,088 | 8/1991 | Ritson et al. | 604/88 |
| 5,092,843 | 3/1992 | Monroe et al. | 604/138 |
| 5,167,641 | 12/1992 | Schmitz | 604/196 |
| 5,300,030 | 4/1994 | Crossman et al. | 604/136 |
| 5,391,151 | 2/1995 | Wilmot | 604/139 |

*Primary Examiner*—John D. Yasko
*Attorney, Agent, or Firm*—Ralph S. Branscomb

[57] ABSTRACT

An injector system utilizes a disposal ampule or, in one instance, a disposal syringe, in all cases being characterized by "tracked" injection wherein the medicament within the ampule or syringe is dispensed as a linear function of needle penetration, and the complete injection operation is executed such that the needle is never exposed. The needle is withdrawn within the medicament chamber after use where it cannot injure anyone except in one instance, in which the needle is capped after the plunger spindle is snapped to prevent reuse of the syringe. The objectives of the improvements are comfort to the patient, ease of use by the administrator and safety for all involved.

6 Claims, 7 Drawing Sheets

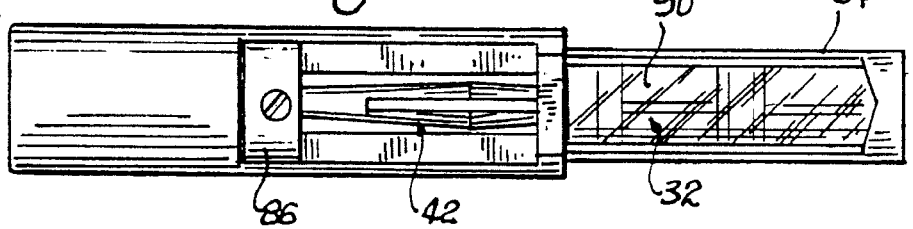
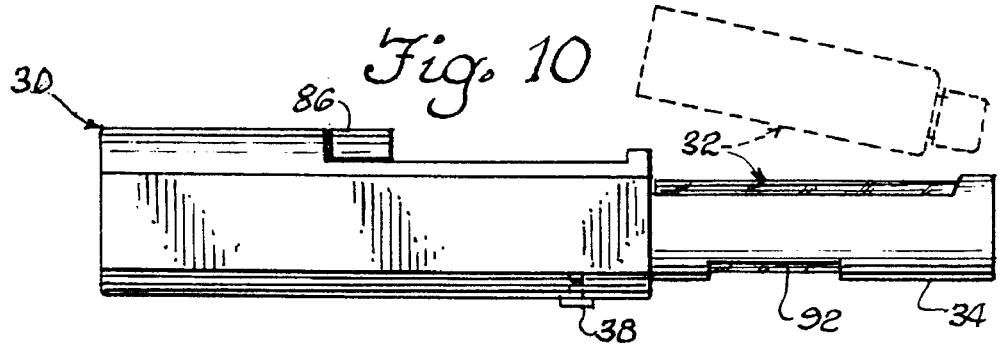
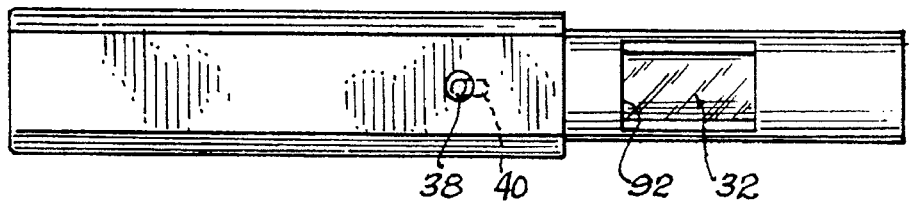
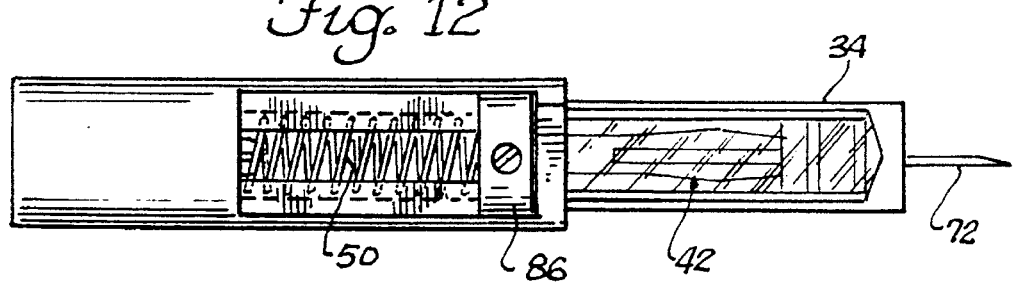
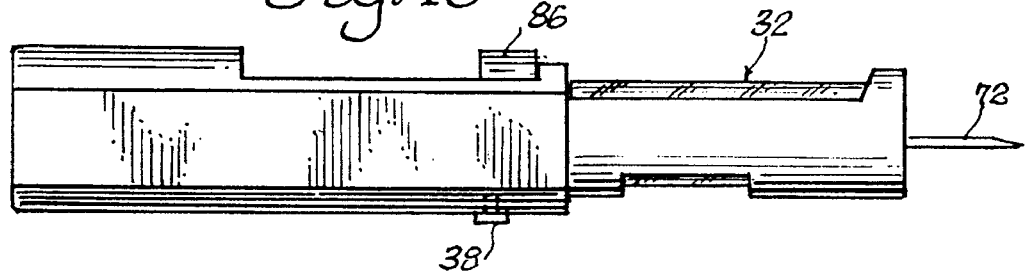

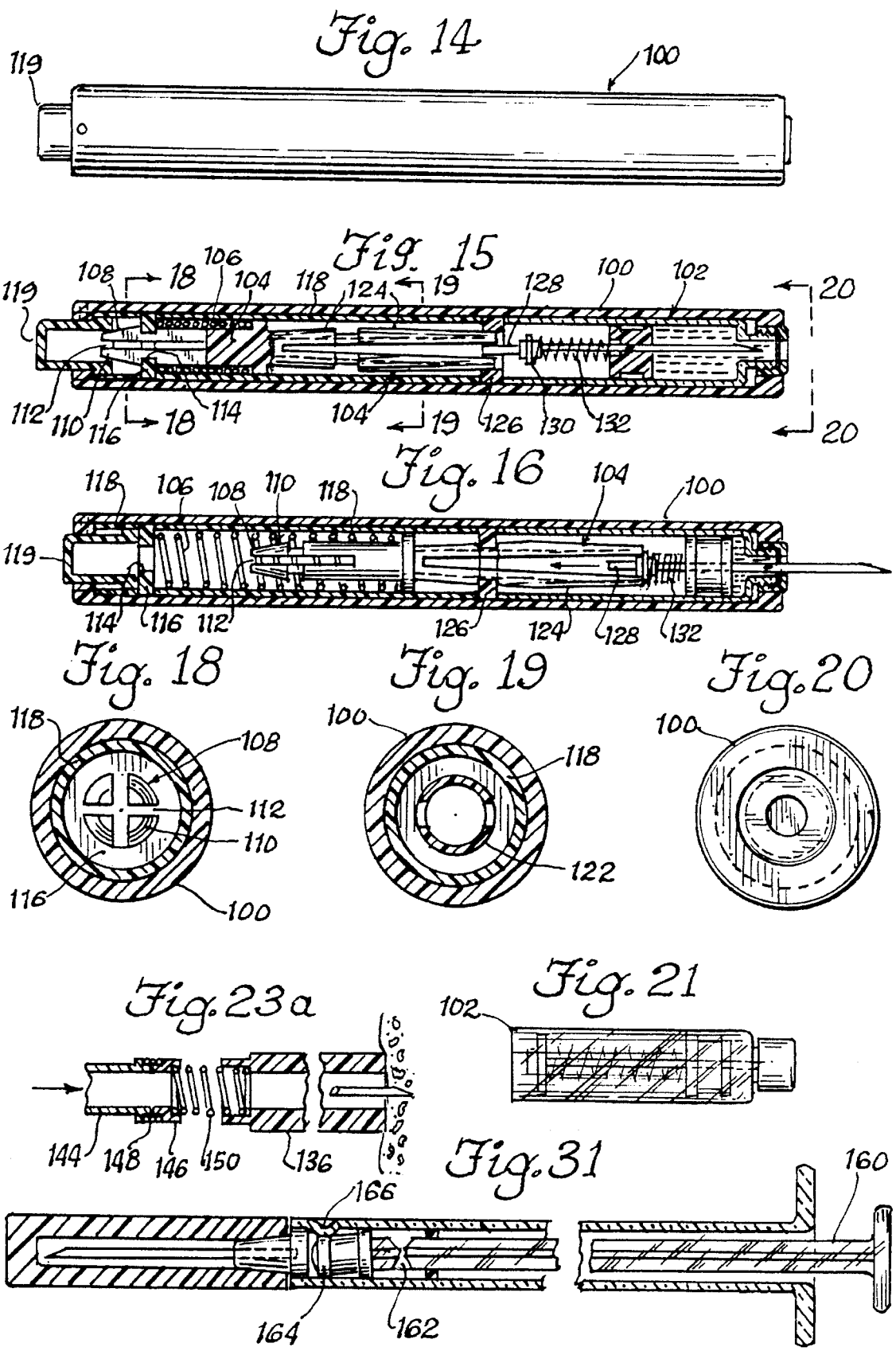

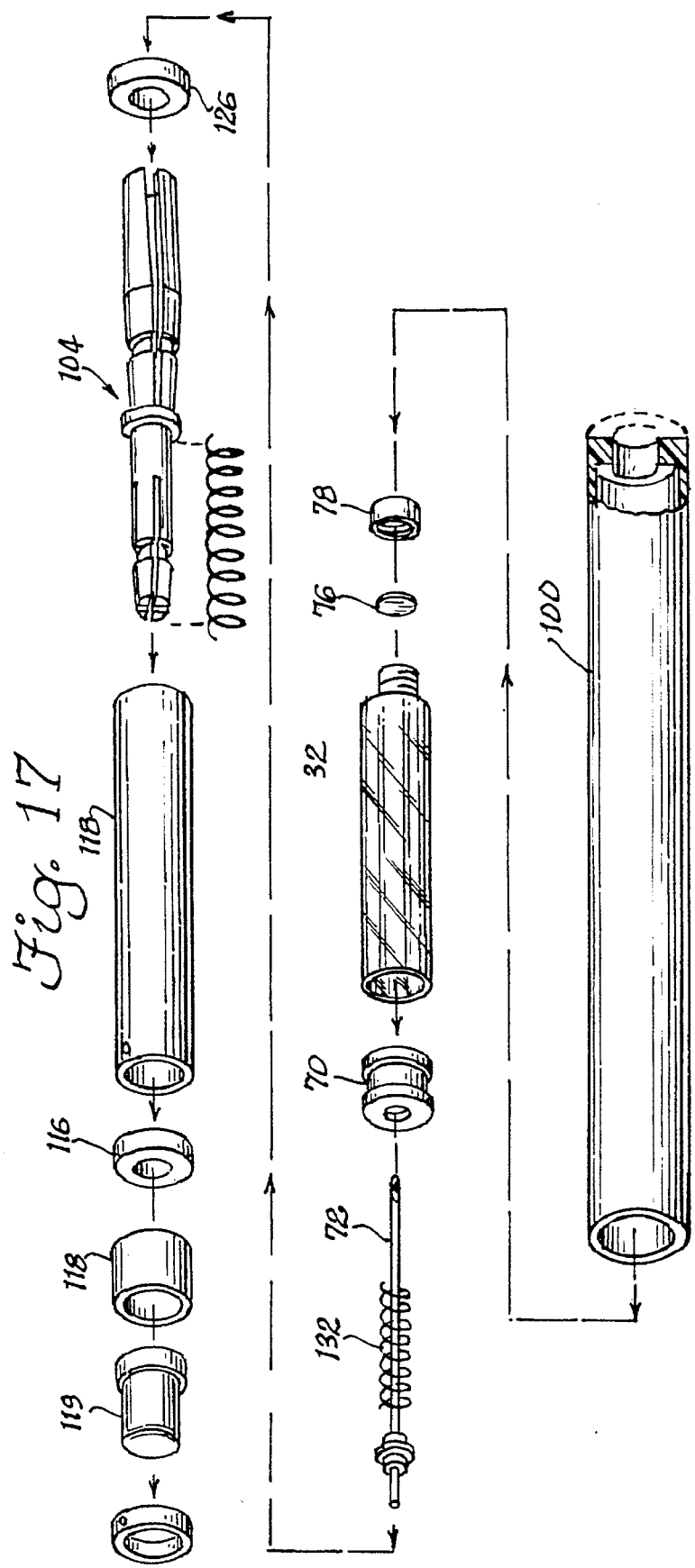

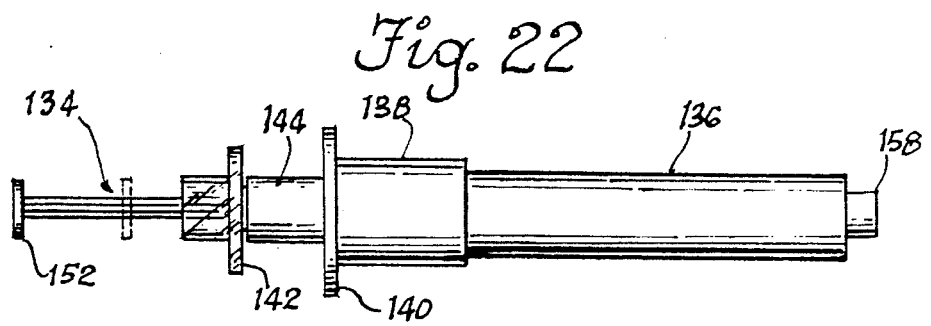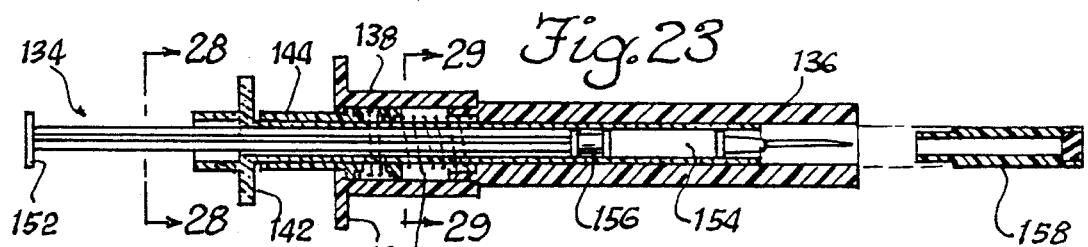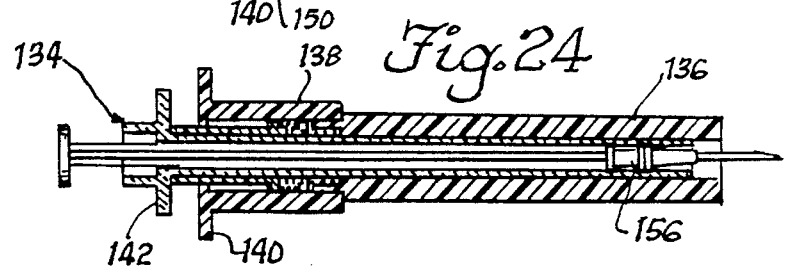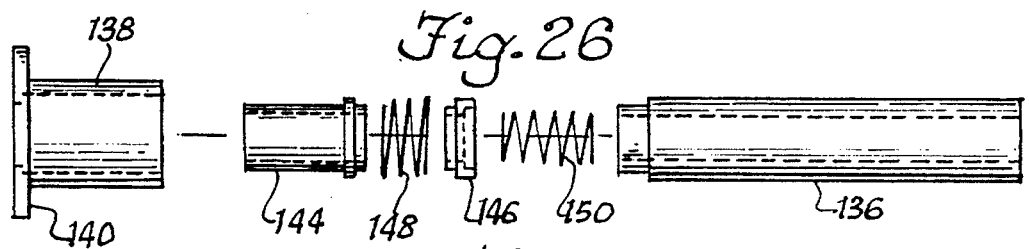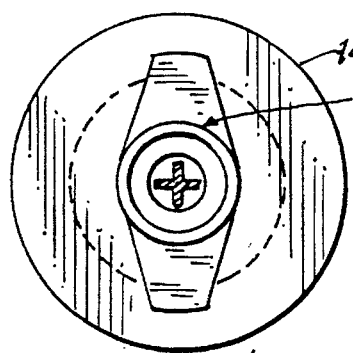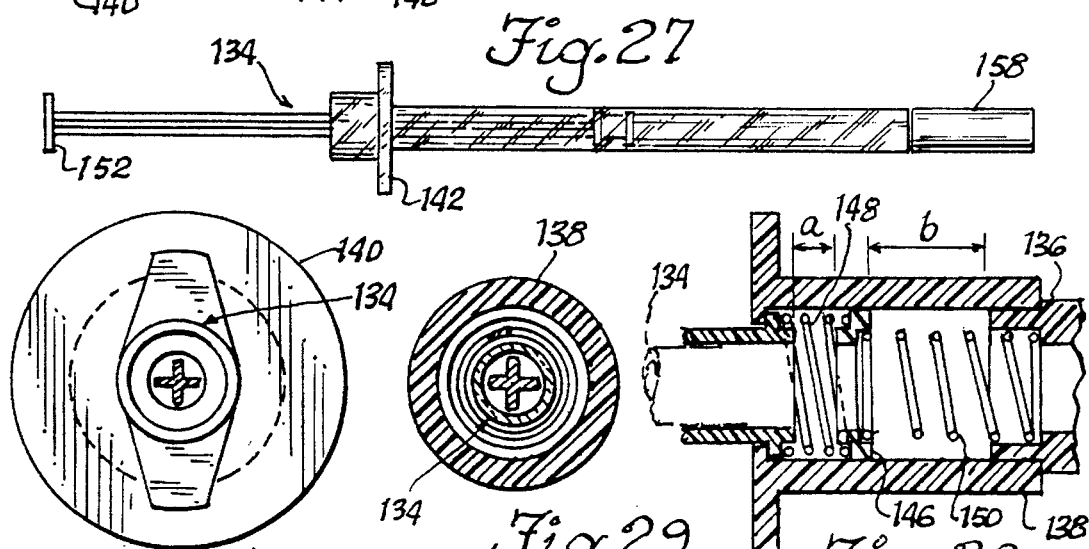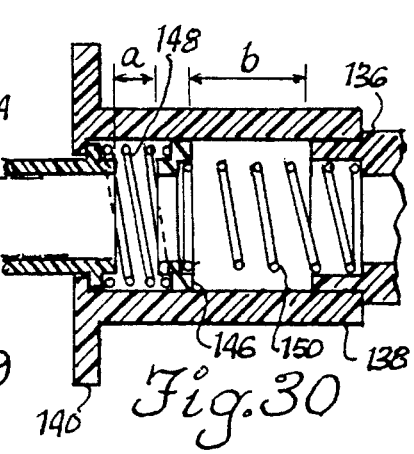

SYRINGE INJECTOR SYSTEM

BACKGROUND OF THE INVENTION

This disclosure is a continuation-in-part of application No. 08/164,330 filed Dec. 9, 1993 on an invention entitled IMPROVED AUTO-RETRACTING NEEDLE INJECTOR SYSTEM, with inventorship common with that of the instant disclosure. The parent application represents a refinement of an AUTO-RETRACTING NEEDLE INJECTOR SYSTEM disclosed in U.S. Pat. No. 5,167,641, issued on Dec. 1, 1992 to William L. Schmitz. All of the mentioned disclosures pertain to injector systems having a needle retracting mechanism to occlude the needle in its entirety subsequent to use of the syringe or injector. The development of such syringes, together with the tracked injector feature dates back to the issuance of the first patent in the name of instant inventor, to Mar. 25, 1980 when U.S. Pat. No. 4,194,505 issued on a CONTAINERIZED HYPODERMIC MODULE. The device of that disclosure comprised a syringe with a needle having a side port which passed into and through a medicament chamber as the plunger was depressed to provide a smooth, linear introduction of the medicament along the needle path concurrently with and proportionately to injection of the needle.

All of the features mentioned above play a part in the instant disclosure. The tracked injection pioneered in the 1980 patent is incorporated in different forms in all of the embodiments disclosed herein. Tracked injection automates a technique which has been manually applied by health professionals when injecting drugs into tissue for timed release into the circulatory system. As the needle is injected from just under the skin to its full depth of insertion, the medicament is dispensed so that rather than forming a pocket or burst of medicament in a "balloon" injection, the fluid is distributed over a longer path. The fluid flow actually parts the tissue in advance of the needle tip, and is more comfortable to the patient than a balloon injection. This technique is standard in dentistry for administering novocain so that the gum tissue is continually numbed during injection before it is penetrated.

A feature inherent in these automated tracked injection devices which cannot in general be duplicated manually, is the application of tactile pressure to the skin by the syringe, beginning before initiation of the injection and continuing throughout the entire injection and retraction cycle. The tactile pressure on the skin has the effect of minimizing the puncture feeling, in some instances causing the patient to miss the sensation of being injected in its entirety due to the comforting feeling of pressure on the skin and the diversion of the nervous system from the actual injection caused by the sensation of pressure. This cannot be done with conventional syringes since the needle does not move relative to the syringe body. This, coupled with the reduction in flesh-tearing by the needle, causes automated tracked injection to be the most painless manner of passing medicament across the derreal barrier yet discovered.

Another substantial advantage attributed to tracked injection is the elimination of the syringe aspiration requirement. Aspiration is routinely done by withdrawing the syringe plunger slightly after full penetration to check for blood, in order to insure that the needle tip is not lodged in a blood vessel. With tracked injection, the medication is spread over the length of the injection path, and cannot all be introduced into the bloodstream even if part of the path crosses one. For this reason, the FDA has approved the use of tracked injection syringes without aspiration.

The syringes of these disclosures are designed to initiate the injection after penetration of the needle tip to a depth of $1/16$ inch. Loss of medicament by premature plunger pressure, a perennial problem with conventional syringes, is not possible since the plunger does not depress until the syringe is against the skin, and initial plunger advance does not inject fluid until the needle tip is sub-dermal.

The tracking syringe of the 1980 patent and most that the inventor has worked on since, have used a disposable ampule with a built-in needle having a side port which enters the medicament chamber as the injector is actuated, causing the simultaneously compression of the fluid and advance of the needle into and through the skin. The needle passes through the rear plug or piston seal of the ampule and out through the front diaphragm. As the side port enters the chamber, the compressive force on the fluid causes it to enter the side port and eject out through the needle tip. Because any further advance of the needle is blocked by the fluid, the arrangement requires distribution of the medicament fluid as a linear function of the advance of the needle, once the side port of the needle communicates with the fluid. This simple system automatically establishes the depth of penetration of the needle and also dictates that the cumulative volume of injected liquid be proportional to the instantaneous depth of insertion of the needle tip during the injection stroke.

In addition to minimizing the pain experienced by the patient, human factors come into play regarding the physical configuration of the syringe or injector. The conventional disposable syringe with its smallish finger tabs and plunger top is adequate for clinical use but may fall short from an ease-of-use stand point in emergency situations, or when used by persons having diminished physical capacity, especially when trying to inject in a hard-to-reach part of the body. This is assuming the patient wants the injection or is willing to receive it, as the problem is exacerbated when the patient is being subdued and is fighting with the administrator and resisting the injection.

In such situations the injection administrator is at times put to extreme effort and sometimes danger when trying to position a disposable syringe on a rapidly moving object and follow the object while depressing the plunger. In instances of insect or snake poisoning or chemical warfare when the nervous system of the self-injecting patient is under attack, there is a need for a simple device which can be quickly pushed against the skin or the clothing outside the skin and easily fired, with the instrument itself taking care of the injection cycle in rapid sequence to insure that all the medicament does in fact enter the patient's body without relying on further efforts of coordination by the victim.

These scenarios of chaos in the injection environment vividly bring to mind the current universally prevalent fear of infection from syringe accidents. The inventor believes that except in unusual circumstances, all syringes should be designed to eliminate the possibility of accidental, or even intentional, injury of health professionals from needle punctures and scratches.

The most foolproof way to eliminate such instances is to design the injection system such that the needle is never exposed at all. The syringe is pressed against the flesh of the patient, the needle enters the patient's body from complete containment within the syringe, the medicament is dispensed, and the needle withdraws completely within the syringe without ever having seen light of day. It is literately impossible, short of syringe malfunction or misuse, for an administrator to receive a needle injury from such a system.

SUMMARY OF THE INVENTION

The several embodiments of the injection system disclosed herein accomplish some or all of the aims set forth above for various types of syringe utilization. All of them have a needle-occluding safety feature and provide tracked injection, with the syringe being pressed against the body of the user. In one embodiment, the syringe is rendered unusable a second time by virtue of a glass spindle-like plunger which snaps at the distal end, at the end of the injection stroke. Another embodiment designed for use repeatedly by health professional and those who must regularly self-inject, utilizes a disposable ampule which comes with a premeasured medicament dose which is quickly and easily snapped into the syringe barrel. This embodiment is actuated by pressure against the patient's skin, which triggers injection and tracked distribution of the medicament. Subsequently a thumb-operated button withdraws the needle within the ampule and opens the barrel to enable the administrator to pop out the old ampule and pop in a new one much as shells are loaded into a shotgun.

Another variation is completely automated and is designed for a single use only. All of the functions are accomplished in sequence and automatically upon the depression of an actuator button at the proximal end of the syringe. This unit is ideal for the aggravated circumstances mentioned above which occur in combat situations, wilderness self-injections and when subduing an unwilling patient. It provides the maximum level of freedom for the administrator by automating the injection cycle in its entirety. The administrator must merely poke or push the distal end of the syringe against the body, and the instant he is finds a satisfactory spot he depresses a button on the proximal end of the syringe similar to a ballpoint pen toggle button, and the needle automatically snaps through the distal end of the syringe into the flesh of the patient, begins dispensing as it penetrates, and then withdraws completely back into the ampule, and the spent unit is discarded in its entirety.

The operating mechanism of these injectors will be clear from the following description in reference to the accompanying drawings.

BRIEF DESCRIPTION OF THE DRAWINGS (#1 of 3 embodiments is illustrated in FIGS. 1–13):

Figure 1:
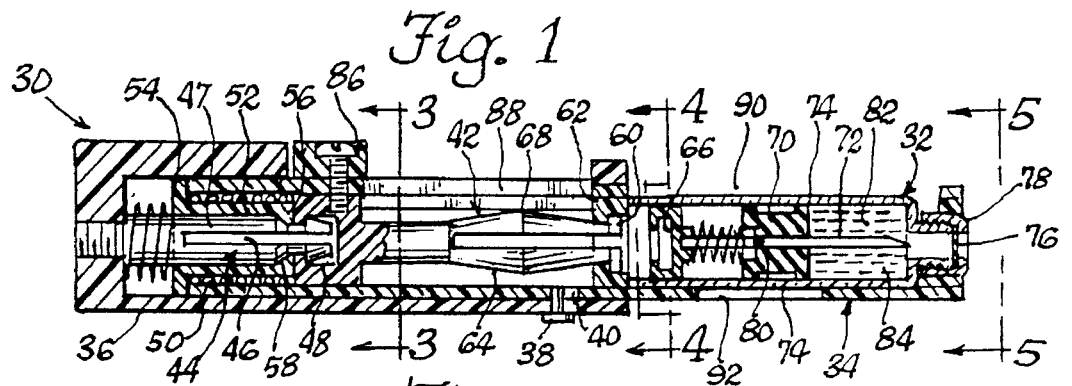
FIG. 1 is a longitudinal section through the first embodiment of my invention which uses disposal ampules, the syringe being shown cocked and ready to fire.
Figure 2:
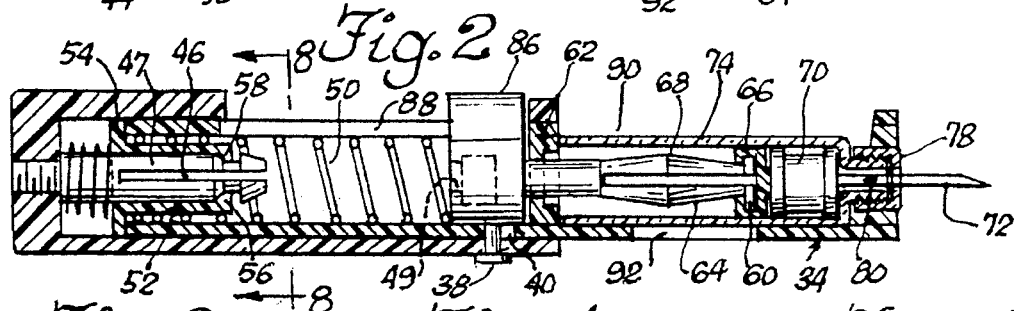
FIG. 2 is a longitudinal section similar to FIG. 1 illustrating the first embodiment in a more advanced stage of its injection cycle in which the medicament is substantially fully dispensed into the patient.
Figure 3:
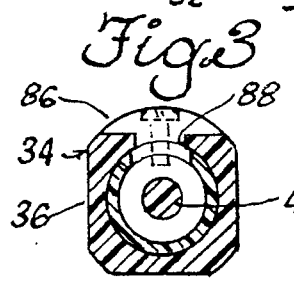
Figure 4:
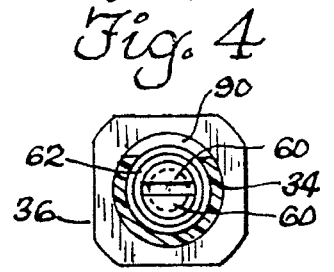
Figure 5:
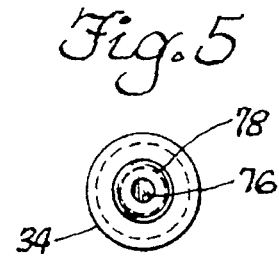
Figure 6:
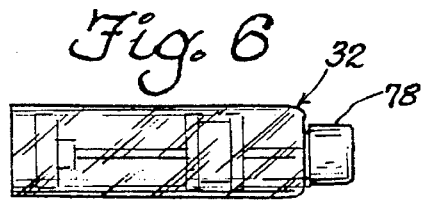
Figure 7:
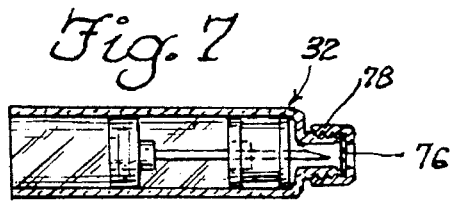
Figure 8:
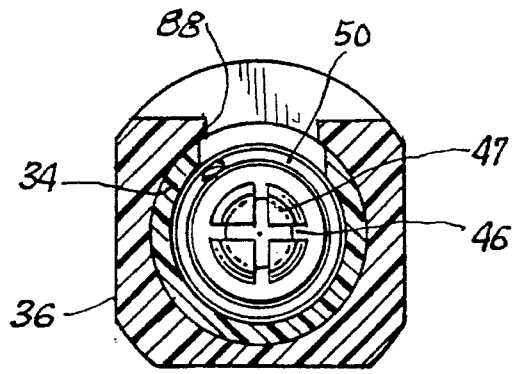
Figure 15A:
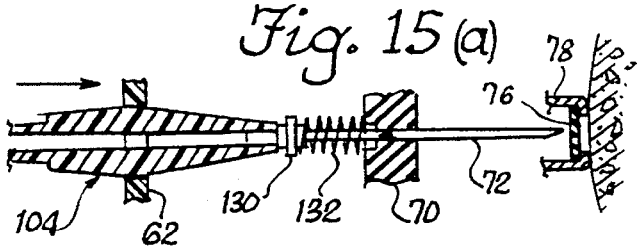
Figure 15B:
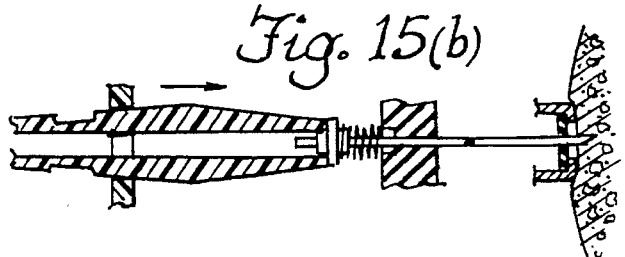
Figure 16A:
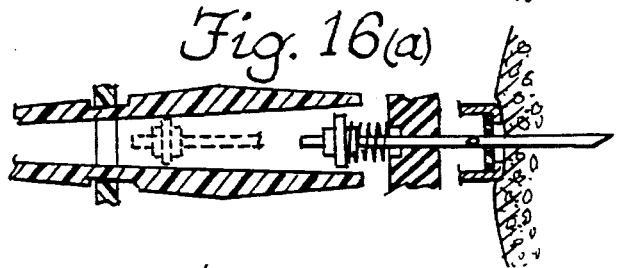
Figure 16B:
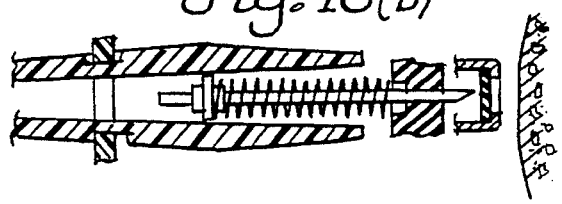

FIGS. 2(a) through 2(g) diagrammatically illustrate the time-sequenced stages of the injection cycle, illustrating the relationship between the distal end of the plunger as it engages, moves forward, moves rearwardly and releases, the rear socket of the disposable ampule;

FIG. 3 is a section taken along line 3—3 of FIG. 1;

FIG. 4 is a section taken along line 4—4 of FIG. 1;

FIG. 5 is a section taken along line 5—5 of FIG. 1;

FIG. 6 is a side elevation view of the disposable ampule of the first embodiment shown prior to use;

FIG. 7 is a section take longitudinally through the ampule of FIG. 6 after the medicament has been fully dispensed and the needle retracted;

FIG. 8 is a section taken along line 8—8 of FIG. 2;

FIG. 9 is a top plan view of the first embodiment of the invention;

FIG. 10 is a side elevation view of my invention illustrating an ampule as it is popped out of the loading chamber;

FIG. 11 is a bottom plan view of the device as shown in FIG. 9;

FIG. 12 is a top plan view of the device of FIG. 9 but as it appears after injection but prior to needle retraction;

FIG. 13 is a side elevation view of the first embodiment in the stage of its injection cycle similar to that of FIG. 12; (The 2nd of 3 embodiments is shown in FIGS. 14–21):

FIG. 14 is the first of a series of figures directed toward the second embodiment of my invention, where in it is illustrated in top plan form;

FIG. 15 is a longitudinal section through the syringe of FIG. 14 as it appears before it is fired;

FIGS. 15(a) and 15(b) illustrate a progression of the distal end of the plunger as its tines are first compressed together to butt up against the needle carriage assembly, and then expand in FIG. 15(b) almost to the point of permitting auto-retraction of the needle;

FIG. 16 is a section taken longitudinally of the second embodiment, similar to that of FIG. 15 but at a point in the injection cycle more advanced wherein the medicament has been fully dispensed;

FIG. 16(a) and 16(b) continue the progression of the operation of the sequence started in FIGS. 15(a) and 15(b) wherein the distal tines of the plunger separate to permit retraction of the needle fully within the syringe into its finally resting place of FIG. 16(b);

FIG. 17 is an exploded perspective of the second embodiment of my invention;

FIG. 18 is section taken along line 18—18 of FIG. 15;

FIG. 19 is a section taken along line 19—19 of FIG. 15;

FIG. 20 is an end elevation view taken from line 20—20 of FIG. 15;

FIG. 21 is a side elevation view of a spent medicament arepule;

(The 3rd and last embodiment of the invention is illustrated in FIGS. 22–31).

Figure 25:
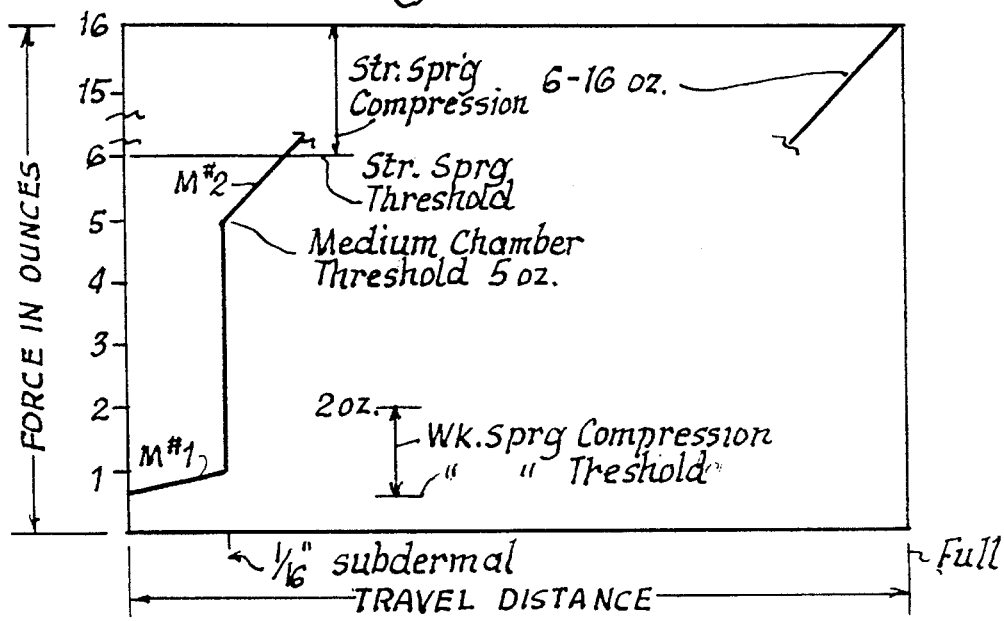

FIG. 22 is an elevation view and is the first of a series of figures illustrating the third embodiment of my invention wherein a conventional disposable syringe is incorporated in a tracked injection shell;

FIG. 23 is a longitudinal section taken through the third embodiment of the invention shown after the syringe has been loaded in the shell but before use;

FIG. 23(a) is a diagrammatic illustration of the compression spring and needle tip injection of the third embodiment as it appears after needle tip penetration but prior to the medicament injections;

FIG. 24 is a longitudinal section taken through the third embodiment similar to FIG. 23 but subsequent to expulsion of the medicament;

FIG. 25 is a graph of the force supplied to the plunger as a function of plunger travel;

FIG. 26 is an exploded elevation view of the invention without the syringe;

FIG. 27 is an elevation view of a typical syringe used in the sleeve of the invention;

FIG. 28 is a section taken along 28—28 of FIG. 23;

FIG. 29 is a section taken along 29—29 of FIG. 23;

FIG. 30 is a longitudinal section taken through the compression spring of the midsection of the third embodiment of my invention; and FIG. 31 is a diagrammatic illustration of an adaptation of the third embodiment of my invention wherein the dispensing plunger self-destructs to prevent reuse of the disposable syringe.

DETAILED DESCRIPTION OF THE PREFERRED EMBODIMENT

This disclosure covers three embodiments of the invention as follows:

1. FIG. 1–13; Semi-automatic disposable-ampule model for heavy repeated use;

2. FIG. 14–21; Fully automatic disposable unit for one-shot emergency use;

3. FIG. 22–31; Tracking sleeve for disposable syringe; minimal configuration.

All three embodiments are slightly different implementations of the same basic inventive concepts discussed above.

The first embodiment, in FIGS. 1 through 13, comprises a reusable unit which is reloaded with a pre-charged ampule for each application. It is semi-automatic. From the cocked position in which it is illustrated in FIG. 1, on pressing the distal end against the flesh of a patient the mechanism is actuated, forcing the needle through the forward diaphragm and into the patient, and beginning tracked fluid injection just after the needle tip is sub-dermal. With the fluid injection completed, the automatic portion of the cycle is finished. The rest of the cycle comprises re-cocking the spring mechanism with the thumb, and popping out and replacing the spent ampule.

This embodiment is intended primarily for use by health professionals and those who must frequently self-inject. It is not for one-time use, but rather for one making injections several times a week up to perhaps several hundred a day. It is very quick to reload, and the ampule portion of the apparatus is the disposable portion and is reduced to the minimum construction of the just the needle, the medicament vial, and the piston or plug which carries the needle. Being triggered by pressure to the forward end, it is extremely convenient for the frequent injector, requiring a little finesse to insure proper positioning before it fires.

The mechanism centers around two different functions. The first is the initial plunger release movement that is caused by pressure to the front of the syringe. The injector has a main body 30 and a disposable ampule unit 32 illustrated in isolation in FIGS. 6 and 7. The main body is comprised of essentially two parts, a barrel 34 which runs virtually the entire length of the unit and the sliding barrel housing 36 which receives the barrel telescopically and freely moves relative to the barrel a short axial distance established by an externally inserted pin 38 which passes through a bore in the housing 36 and then rides in a longitudinally extended slot 40 in the barrel. This slot permits the axial play necessary to fire device when the barrel and its housing must be mutually axially compressed such as by pressure on the end of the barrel provided by a patient's flesh.

The initiation of the firing stroke is controlled by the trigger mechanism in the left end of the device as illustrated in FIGS. 1 and 2. The spindle-like plunger 42, which will snap forward and power the needle into the patient upon actuation, is retained rearwardly by the four-quartered, flower-shaped compressible detente 44. Bisecting slots 46 cut through the polymeric material enable the forward detente ears 48 to be compressed. As can be seen in FIG. 1, these ears are engaged in socket 49 of the proximal end of the plunger, and until they are compressed together to release the plunger it is retained in the cocked position shown in FIG. 1. Were these ears to be compressed together however, the slots 46 provide adequate radial travel distance to free the ears of the socket walls of the plunger, permitting it to snap forward under action of the relatively highly compressed spring 50 which encircles the actuator sleeve 52 riding on the body of the detente 42. The actuator sleeve 52 has an annular flange 54 at its rear termination which captures the proximal end of the compression spring, the distal or forward end of which presses directly against the rear end of the plunger structure.

Figure 1A:
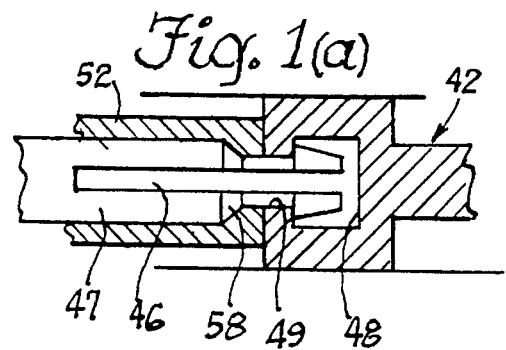
FIG. 1(a) is a diagrammatic illustration of the plunger release mechanism while it is cocked, prior to release.
Figure 1B:
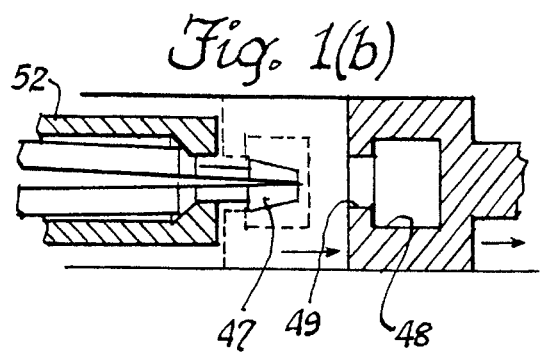
FIG. 1(b) is a diagrammatic illustration of the mechanism of FIG. 1(a) at a further advanced point in time, subsequent to the release of the plunger.

The actuator sleeve 52 has an inwardly directed annular lip 56 which substantially conforms to the sloped annular shoulder 58 of the detente 44. In the orientation shown in FIG. 1, the actuator sleeve has substantially no effect on the four separate tines which together constitute the detente 44. However, if one were to grasp the barrel housing 36 and press the barrel 34 against a patient, the proximal end of the barrel would depress the annular flange 54 of the actuator sleeve 52, causing the lip 56 to compress the four tines 47 into the slotted voids 46, reducing the composite diameter of the detente head such that it slips through the socket opening 49. Because only the detente holds the plunger against the substantial force of the injection spring, the instant the plunger socket is free of the detente head, it springs forward. The first position and subsequent released of the plunger are diagrammatically illustrated in FIGS. 1(a) and 1(b), respectively.

On being released, the plunger darts forward. Its forward end has a set of four hook-like feet 60 which operate in manner very similar to the four-line detente 44. In the cocked rest position shown in FIG. 1, these feet rest inside a plunger control ring 62, which is really a baffle defined in the barrel member with a cylindrical axial bore therethrough. The diameter of this ring and the sculpted exterior surfaces 64 act together to control the separation of the feet 60 as a function of axial progression of the plunger through the ring.

Figure 2A:
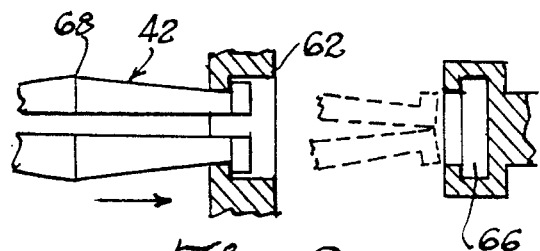
Figure 2B:
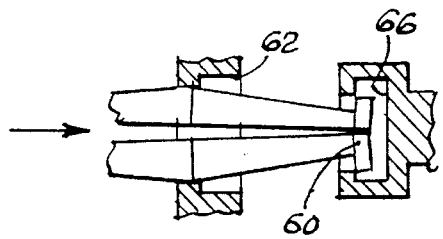

From the position of FIG. 1, the plunger begins to move forward to execute the automated portion of its cycle which is diagrammatically illustrated in the FIGS. 2(a) through 2(f) drawing sequence. Beginning in the stable, cocked position of 2(a), the plunger moves forward through the control ring 62, causing the feet to compress together as shown in FIG. 2(b). At the same time that they are moving forward they move into the socket 66 defined in the rear end of the ampule, and as the central ridge 68 passes through the ring, the feet are permitted to expand again, defining a positive grip inside the socket 66 so that now the plunger can move the ampule in either axial direction.

Figure 2C:
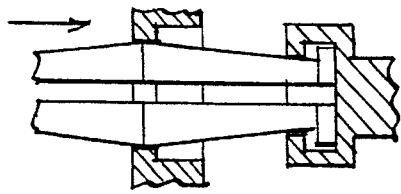
Figure 2D:
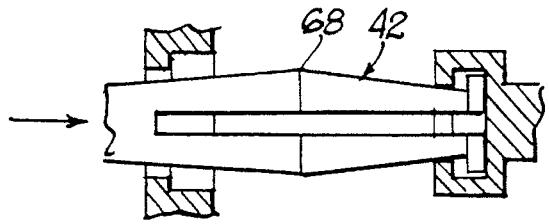
Figure 2E:
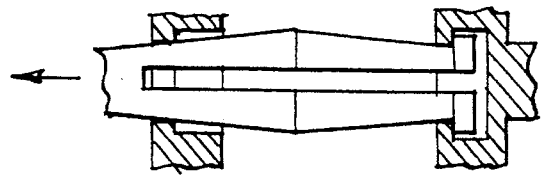
Figure 2F:
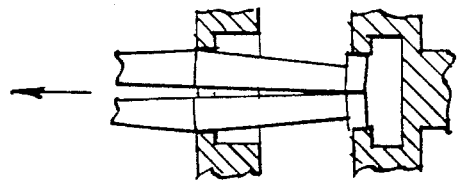
Figure 2G:
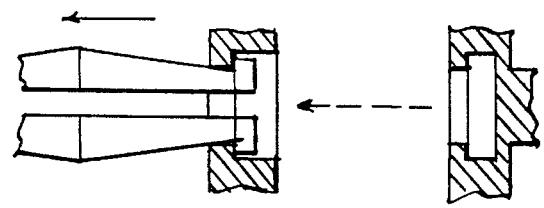

This positive engagement having been effected in FIG. 2(c), the plunger now continues to move forward under the power of the spring 50. The stage of the injection cycle illustrated in FIG. 2(c) corresponds to engagement of the plunger into the ampule socket at the very beginning of the injection stroke. Continued forward motion of the plunger from the position of 2(c) to 2(d) operates the second operative mechanism of the syringe, which is the ampule injection system. The ampule has a rear plug or piston 70 which carries the needle 72 and supports it in proper axial alignment. The piston also seals against the side wall 74 of the ampule and is initially butted up against the socket member 66. As the plunger begins to move the socket member and the abutted piston forward from the starting orientation of FIG. 1, the needle tip begins to penetrate the diaphragm 76, which covers the front end of the arepule and is retained thereon by end cap 78. A side opening 80 in the needle 72 begins its stroke inside the material of the piston 70 and thus there is no passageway for medicament to pass through to the opened front tip of the needle until the needle has traveled a certain distance, which corresponds to the distance needed to penetrate 1/16 inch into the patient's skin. At this point, the location of the side opening is coordinated with the ampule structure such that, now that the needle tip is securely under the skin, medicament begins its forced flow forwardly through the needle body.

An examination of FIG. 1 makes it clear that once the needle reaches the subdermal stage, the only way it can move forward is by displacing the medicament fluid 82 out of the medicament chamber 84 defined by the ampule. Conversely, the only way the fluid is going to be injected is by the forward motion of the piston, so that for each linear unit forward that the needle travels, a certain unit volume of fluid is displaced from the medicament chamber out through the needle tip. In a very linear fashion, a controlled and uniform distribution of medicament along the injection path of the needle is achieved. The axial positioning of the side aperture in the needle is coordinated with the ampule design such that no medicine is wasted prior to actual penetration of the needle into the flesh. No communication is made until after initial penetration.

The final resting position of the syringe is shown in FIG. 2. The needle is extended to the its farthest throw, ordinarily about ⅝th inch. This represents the end of the automatic cycle. The injection has been made and the needle is still embedded in the patient. It is retracted by a thumb-operated button 86 which is shown screwed in the top of the socket portion of the plunger 42, but would be integrally molded with the plunger in production. This button rides along an axially extended slotted aperture 88, traveling freely between the extremities shown in FIGS. 1 and 2.

The dose administrator would generally engage the barrel housing 36 with his/her right hand and pull the thumb button 86 back to the cocked position, at which point the plunger socket snaps over the head of the detent, and the mechanism is back where it started, with one exception: it now has a spent arepule in the barrel rather than a fresh one.

As shown in FIG. 10, the barrel has a large ampule access opening 90 at the top, and a finger pop-out opening 92 on the lower side. The action of the arepule as it is snapped in and out of the barrel is very crisp and the ampule seats very snugly within the barrel. Ampules can be popped in and out of the barrel all day long and the thumb button operated to recharge the spring hundreds of times without undo hand or finger fatigue.

Whereas this first-described embodiment is intended for those who inject on a regular basis, the following model, shown in FIGS. 14 through 21, is intended for a single use only, subsequent to which it is discarded. Because it is a relatively complex mechanism for a disposable, its price would be high for professionals who would use it on a regular basis, or by a regular self-injector such as a diabetic. It is designed strictly toward a single, very important shot made under circumstances which could very well be far from optimal for executing such procedures, such as injecting belligerent mental patients or self-injecting under conditions of partial neural collapse. If it works, the $10 price tag will not be an issue.

The mechanism is similar in principle to that of the first embodiment but implemented differently. A tubular barrel 100 runs the entire length of the syringe, housing an ampule 102 in the forward end and the plunger 104 in its mechanism toward the rear. Similar to the first embodiment, a highly compressed coil spring 106 provides the motive power for the plunger and is retained in its compressed mode by action of the three-dimensional T-shaped head 108 of the four-split sleeved detente 110, the compressible quarter-heads of which displace into the slotted voids 112 to permit passage of the detent head through the opening 114 of a restraining washer 116 captured between the butted ends of the spacer sleeves 118. Compression of the quarter-heads together is effected by thumb action on the end cap/actuator 119 which has the predictable compressing effect on the head 108 of the detent as it is pressed into the barrel, releasing the detent to pass through the opening 114, freeing the injection spring for limited but rapid expansion, powering the plunger 104 forward.

The plunger 104 is of a very controlled construction. It extends as a unitary piece from the proximal detent 110 to the distal ends of the semi-cylindrical split sleeves 122 defining the operative end of the plunger. The outer surfaces 124 of the plunger split sleeves are carefully contoured to cooperate with the aperture in the guide ring 126 to execute the motion illustrated in the FIGS. 15(a), 15(b), 16(a), and 16(b). An added automatic step is provided beyond the steps of the first embodiment because this unit is totally automatic, starting with a cocked syringe loaded with a pre-measured dose of medicament and ending with a spent ampule and ending with a needle completely withdrawn inside the ampule chamber. Starting with the orientation of FIG. 15, on depression of the actuator button the plunger snaps forward with the split sleeves being compressed to a converging configuration illustrated in FIG. 15(a). This configuration of the front tips of the split sleeves enable them to engage around the rearwardly extended end of the needle 128, or a small nib extending in line with the needle, and press against the circular baffle 130. The baffle is of limited diameter so that the split sleeves must be converged in order to push forwardly against it. The nib 128 acts a guide.

With the semi-cylindrically split sleeve tips converged together, the plunger continues to press the needle carriage in a single, smooth motion all the way to the end of its injection stroke. As with the first embodiment, the construction of the needle and its side opening relative to the piston and the rest of the arepule cause the needle to penetrate the skin before injecting any fluid, and thereupon initiates the linear, uniform injection of medicament throughout the needle stroke.

As the plunger moves forward under the powerful force of the compression spring at the rear of the syringe, the light-weight spring 132 is compressed. At the end of the injection stroke the syringe is oriented as illustrated in FIG. 16. However, it does not stay in this configuration even for an instant as the expanding split sleeves, which are permitted to expand under their own structural tension by the passage of the wider part of the plunger surface through the guide ring and out the other side, are popped radially outwardly beyond the radius of the baffle 130 as shown in FIG. 16(a) freeing the needle carriage, under action of the spring 132 to withdraw inside the ampule into the final resting position shown in FIG. 16(b).

With the actuation of a single thumb operated button, within a split second the entire operation is executed and complete, and the syringe is ready for disposal. Hopefully, the patient is not.

The embodiment of FIGS. 14 through 21 in a sense represents the final solution. It incorporates all the advantages and features that the inventor has been working on for the past 15 years in a single unit. Its multiply reversing automatic action is smooth, quick and effective. The shape of the syringe and the location of the actuator button make it possible to reach around to virtually any part of the body for self-injection and with complete control of the syringe press it against the flesh and push the button with a thumb, finger or even an adjacent tree trunk to initiate the virtually foolproof action sequence resulting in the full injection of the measured dose of medicament. But for the relative expense of producing this embodiment, it would likely replace all others.

Turning now to the third embodiment, if the second embodiment is the top of the line, the third embodiment is the bottom. It merely converts a conventional syringe into a tracked injection syringe with automatic needle retraction from the patient, but not back inside the syringe body. A re-use disabler is provide as an option.

As shown in FIGS. 22 through 30, the invention itself is a sleeve composed of several parts as illustrated in FIG. 26, and into the sleeve is inserted a conventional syringe shown in FIG. 27 at 134. The invention comprises a barrel 136 at the distal end in a surrounding collar 138 which has an annular flange 140 which is used as the finger tabs in place of the fingertabs 142 on the syringe itself. The barrel and the collar are fixed together whereas the remaining two parts other than springs, the sleeve 144 and the spring separator seat 146, are free to migrate axially along the syringe which they slip over. Between these respective parts is a first, weak spring 148 and a second strong spring 150.

Turning to FIG. 23, it can be seen that as the thumb presses the plunger platform 152 of the syringe and the index and middle fingers engage the flange 140 of the collar and compress these two parts together, something in the syringe is going to have to move axially relative to adjacent structure.

Because the weak spring 148 has only two ounces of fully compressed spring force and the strong spring begins with a resistance of about 6 ounces, the weak spring compresses first. The compressive throw "a" as illustrated in FIG. 30 that the little spring permits before it is completely collapsed corresponds to the amount of travel required of the needle tip in order to make its subdermal entry into the patient 1/16 inch without injecting. Also, the resistance of the two springs is coordinated with, first, the sliding resistance of the syringe in the outer barrel, and second the resistance of the medicament chamber 154 and the piston 156 to penetration and fluid expulsion. The sliding resistance of the syringe in the sleeve is less than the maximum resistance of the weaker spring, and the injecting resistance is greater than the 2-ounce force of the weak spring but about the same as the initial opposing force of the strong spring, about 6 ounces.

The operational result of these relative resistance and spring strength assignments are illustrated in the graph in FIG. 25. As the force on the plunger begins, the small spring begins to compress and at first there is no movement at all. Then, as the opposing force of the weak spring builds throughout its compressive stroke, it is designed to surpass the threshold resistance of the syringe inside the outer barrel, causing it to slide forwardly relative to the barrel and move the needle tip forward until it pierces the skin 1/16 inch. This motion is indicated at "M #1" in FIG. 25. At this point the small spring is fully compressed and the needle is just inside the skin and further advance of the plunger pauses pending elevation of the compressive force enough to cause injection of medicament into the tissue and needle penetration deeper into the flesh.

Continued elevation of thumb pressure raises the force to equal the combined resistance to fluid expulsion of the medicament chamber, resistance to flesh penetration of the needle and sliding resistance of the syringe in the barrel. This force is indicated as the "medicament chamber threshold 5 oz." in FIG. 25. The plunger moves the syringe, which has already penetrated the skin, and begins to force the plunger forward in the syringe barrel to inject the medicament as the needle penetrates. This continues as indicated at "m #2" in the drawing until full travel of the needle and injection of the medicament is complete. Injection begins at the approximate same force level required for the initial compression of the strong spring, which increases as the spring is compressed. as the syringe moves in the outer sheath and the plunger moves in the syringe, for smooth tracked injection. At the end of the stroke the syringe ears butt against the finger tabs of the carrier so that no more forward motion of the syringe is possible, coinciding with the leading end of the syringe body being flush with the end of carrier barrel. The strong spring is now fully compressed.

The injection being complete, the administrator releases the plunger. Both springs are fully compressed. Withdrawal of the needle from the flesh offers much less resistance than forcing the tissue apart and injecting the fluid into the previously solid flesh, and is easily handled by the strong spring force until the strong spring is fully expanded at the 1/16 inch trans-dermal point. Then the weak spring continues for at least part of its full extension, which is enough to draw the needle completely inside the barrel. While so withdrawn, it is covered with the cap 158 prior to removal from the carrier for disposal.

It will be noted that the principal of tracked injection exhibited in the third embodiment differs from the first two. In embodiments one and two, a forced linear correlation exists between the cumulative fluid injected and the travel distance of the needle point. This forced correlation is not present in the embodiment just described, so that the spring tensions must be adjusted experimentally until an approximate linearity is achieved. Generally speaking, since the springs retard sliding of the syringe barrel spring strength is roughly proportional to the ratio of injection over penetration.

Whereas in the prior embodiments, where $M_v$ is Medicament volume and I is needle injection distance, $$\Delta M_v = k\Delta I,$$

in this last embodiment, where "F" stands for spring force, "S" is Syringe barrel travel distance in the outer sleeve and "P" is injecting piston instantaneous resistance, the following is approximately true:

$$F = \Delta S/P_r$$

In other words injection distance is tied to injected fluid volume in the first two embodiments, but only a rough proportionality between syringe movement vs. needle travel is present in the last embodiment with no tying of injected volume to needle travel.

The last-discussed embodiment, #3, also failed to provide for needle withdrawal to a safe place inside the syringe medicament chamber. Although the needle is injected, withdrawn and capped in an completely unexposed cycle, it would nonetheless be possible to remove the cap and use the syringe again, risking the transfer of biological hazards.

To eliminate this possibility, the syringe can be manufactured so that it self-destructs after a single injection. FIG. 31 illustrates one manner of accomplishing this wherein the syringe plunger 160 is a single integral piece of glass with a converged, weakened neck 162 just behind the bulbous distal end 164. The inner wall of the syringe is cylindrical all the way down except at the very end, where one or both walls suddenly deflect as indicated at 166. As the plunger is forced down, this deflection breaks the delicate neck at the reduced diameter breakpoint, rendering the plunger incapable of withdrawing the medicament chamber piston to aspirate fluid. A similar configuration could be used to break the needle instead of the plunger.

With these improvements, mixed and matched as described to fit various manners of use, it is difficult to conceive of any left that could be improved upon. The safety, comfort, and simplicity of use of these improved syringe systems does not leave much to be fixed. Because of the relatively low operating costs and ease of use it is anticipated that the first embodiment, the semi-automatic frequent user model will be the easiest to commercialize, but that niche market exist for the other two embodiments as well, with all three together representing a complementary product line seemingly covering the needs of anyone involved with syringe injections.

LIST OF NUMBERED ELEMENTS

| | |
|---|---|
| 30. | Main Body |
| 32. | Ampule |
| 34. | Barrel |
| 36. | Barrel Housing |
| 38. | Pin |
| 40. | Slot |
| 42. | Plunger |
| 44. | Detent |
| 46. | Bisecting Slots |
| 47. | 4 times |
| 48. | Socket of Plunger |
| 49. | Socket Opening |
| 50. | Spring on Detent |
| 52. | Actuator Sleeve |
| 54. | Actuator Flange |
| 56. | Annular Lip-inwardly directed |
| 58. | Shoulder-Sloped |
| 60. | Detent Feel |
| 62. | Plunger Control Ring |
| 64. | Outer Surface of Plunger |
| 66. | Socket in Ampule |
| 68. | Central Region of Plunger |
| 70. | Piston |
| 72. | Needle |
| 74. | Sidewall |
| 76. | Diaphragm |
| 78. | Cap |
| 80. | Side Opening in Needle |
| 82. | Fluid |
| 84. | Medicament Chamber |
| 86. | Thumb Button |
| 88. | Thumb Button Clearance Slot |
| 90. | Ampule Access Opening |
| 92. | Pop-Out Opening |
| 94. | RESERVE |
| 96. | RESERVE |
| 98. | RESERVE |
| Begin Emb. #2; FIGS 14–21 | |
| 100. | Barrel |
| 102. | Ampule |
| 104. | Plunger |
| 106. | Coil Spring |
| 108. | Head of Detent |
| 110. | Detent |
| 112. | Slot |
| 114. | Opening for Detent Head |
| 116. | Restraint Washer |
| 118. | Spacer Sleeves |
| 119. | Actuator Button |
| 122. | Cylindrical Times |
| 124. | Exterior Guides Surfaces of Semi-cylindrical Tines |
| 126. | Guide Ring |
| 128. | nib of Needle |
| 130. | Baffle on Needle |
| 132. | Spring |
| Begin Emb. #3 - FIGS. 22–30: | |
| 134. | Conventional Syringe |
| 136. | Barrel |

LIST OF NUMBERED ELEMENTS -continued

| | |
|---|---|
| 138. | Collar |
| 140. | Flange |
| 142. | Syringe Finger Tabs |
| 144. | Sleeve |
| 146. | Spring Separator Seal |
| 148. | Weak Spring |
| 150. | Strong Spring |
| 152. | Plunger Thumb Platform |
| 154. | Medicament Chamber |
| 156. | Piston |
| 158. | Cap |
| Break Away Piston Embodiment: | |
| 160. | Plunger |
| 162. | Weaken Neck |
| 164. | Bulbous distal end |
| 166. | Deflection Ramp |

I claim:

1. An automatic injection apparatus for use the powered injection of medicament comprising:

(a) an elongated cylindrical barrel defining a forward end and a rear end;

(b) a medicament chamber housed in said barrel substantially coaxially with said barrel and being defined by a cylindrical wall, a front diaphragm and a piston slidable in said cylindrical wall spaced behind said diaphragm;

(c) a hollow hypodermic needle coaxially slidably seated in said piston and having a forward flesh-penetrating outlet tip and a rear end mounting a transverse baffle, and a side inlet intermediate said baffle and tip which is disposed rearwardly of the forward face of said piston prior to use of said apparatus;

(d) a plunger disposed in axially slidable relation in said barrel behind said medicament chamber and being operable to slide forwardly from a cocked position, to a forward injected position and back to said forward position;

(e) a power spring biasing said plunger from said cocked position forwardly in said barrel to engage said baffle and having adequate strength and throw to displace said needle forwardly to pierce said diaphragm and enter the flesh of a patient to a predetermined depth, at which point said baffle butts against said piston and forces same forwardly such that said medicament is forced through said side inlet into said needle and out said outlet tip into the flesh of the patient to purge said medicament substantially completely from said chamber throughout an injection stroke such that medicament is injected continuously substantially as a liner function of increasing depth of injection of said needle tip in a tracked injection; and, (f) detent means to lock said plunger in said cocked mode against the tension of said spring, and an externally accessible release means to neutralize said detent means and release said plunger to execute said injection stroke.

2. An automatic injection apparatus according to claim 1 and including an ampule disposed within said barrel and said ampule defines said medicament chamber.

3. An automatic injection apparatus according to claim 1 wherein said apparatus includes automatic needle retraction means which includes a retract spring disposed between said piston and said baffle for powering said needle into a retracted mode to withdraw said needle within said chamber when said injection stroke is complete.

4. An automatic injection apparatus according to claim 3 wherein said plunger has a plurality of radially spaced and compressible split sleeves defining the forward end thereof, and a guide ring axially fixed in said barrel, said split sleeves passing through said guide ring and together defining a common external transverse cross section which radially expands rearwardly from the front ends of said sleeves, ramping up to an apex and then back to a diameter reduced from the apex diameter, such that as said split sleeves move forwardly through said ring from the cocked mode said sleeves increasingly converge at the forward ends thereof and displace said baffle and needle forwardly until said injection stroke is complete, at which point said apex has passed through said ring and said sleeves are expanded beyond the diameter of said baffle, permitting said baffle to pass rearwardly between said split sleeves as said needle snaps back into said medicament chamber powered by said retract spring.

5. An automatic injection apparatus according to claim 3 wherein said apparatus is intended for a single emergency use and said medicament chamber is defined as an ampule inextricably contained within said barrel and disposed of therewith.

6. An automatic injection apparatus according to claim 4 wherein said barrel has an actuator button defined in the rear end thereof which when depressed axially forwardly actuates said release means such that the administrator has only to locate the forward end momentarily in an injectable area and depress the button and a complete cycle from injection through retraction of the needle into said medicament chamber is executed.

* * * * *